United States Patent
Nobbe et al.

(10) Patent No.: US 7,462,160 B2
(45) Date of Patent: Dec. 9, 2008

(54) DYNAMIC ROTARY ORTHOTIC CONTROL SYSTEM

(76) Inventors: Ralph W. Nobbe, 3810 State St., Santa Barbara, CA (US) 93105; Erwin A. Nobbe, 817 Arguello Rd., Santa Barbara, CA (US) 93103

( * ) Notice: Subject to any disclaimer, the term of this patent is extended or adjusted under 35 U.S.C. 154(b) by 452 days.

(21) Appl. No.: 11/191,706

(22) Filed: Jul. 27, 2005

(65) Prior Publication Data
US 2007/0027421 A1 Feb. 1, 2007

(51) Int. Cl.
*A61F 5/00* (2006.01)
(52) U.S. Cl. .................. 602/27; 602/5; 602/23
(58) Field of Classification Search ............ 602/5, 602/12, 16, 23, 27–29, 65; D24/190, 192; 128/882
See application file for complete search history.

(56) References Cited

U.S. PATENT DOCUMENTS

| | | | | |
|---|---|---|---|---|
| 5,282,483 A | * | 2/1994 | Wang | 128/882 |
| 5,593,383 A | * | 1/1997 | DeToro | 602/27 |
| 6,146,344 A | * | 11/2000 | Bader | 602/6 |
| 2005/0038365 A1 | * | 2/2005 | Scott | 602/23 |
| 2005/0234378 A1 | * | 10/2005 | Ingimundarson et al. | 602/23 |

* cited by examiner

*Primary Examiner*—Kim M Lewis
(74) *Attorney, Agent, or Firm*—Koppel, Patrick, Heybl & Dawson; Michael J. Ram

(57) ABSTRACT

An orthotic device includes a composite strut, a footplate removeably attached to a lower end of the strut, an upper tibial cuff removeably attached to an upper end of the strut and a lower tibial cuff removeably attached to a central portion of said strut. The footplate, upper tibial cuff and lower tibial cuff are formed of a composite material, preferably a carbon fiber composite. Each of the footplate, upper tibial cuff and lower tibial cuff include a support structure molded into the component with threaded holes therein. The upper and lower end of the strut may also include mounting holes therein for bolting the upper tibial cuff and footplate thereto. Mounting structure may also include mounting plates positioned on the rear surface of the strut and one or more tapered wedges mounted between the mounting structure on a rear of the strut, said tapered wedges allowing an angled orientation of the footplate and cuffs in relationship to the surface of the strut to which it is attached.

25 Claims, 8 Drawing Sheets

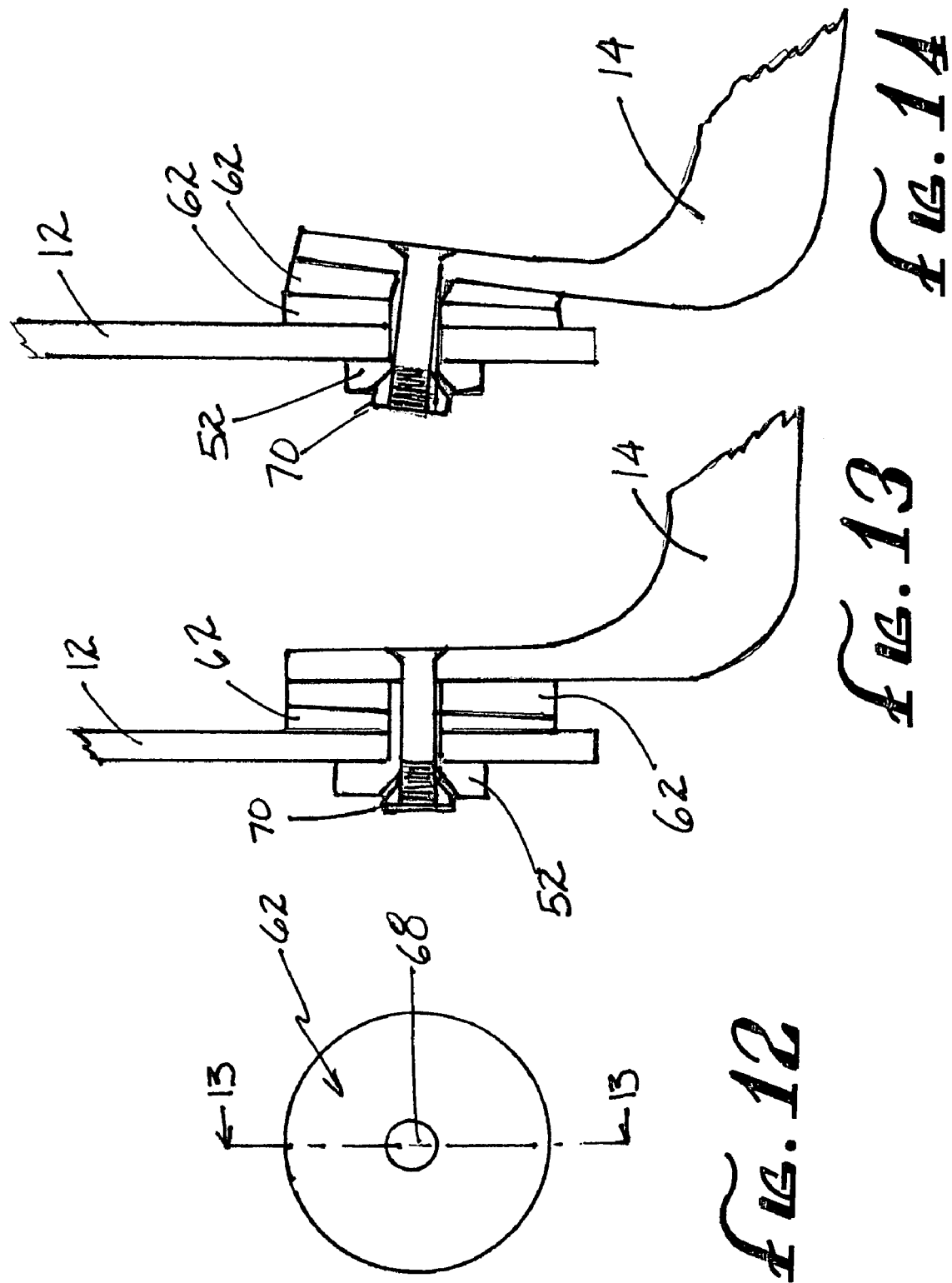

DYNAMIC ROTARY ORTHOTIC CONTROL SYSTEM

This application is directed to an ankle foot orthotic device component system (AFO), referred to as a Dynamic Rotary Orthotic Control System (DROCS), designed to assist patients with neuromuscular impairments. The DROCS consists of a composite strut component placed upon the posterior side of the leg and attachment hardware securing the multiple individual components of the system to the strut which allows the device to be readily adjusted to fit and be adapted to meet each patient's particular stature and rehabilitation requirements.

BACKGROUND

There are various techniques and numerous prefabricated models available for post-operative application. However, none have a dynamic composite strut assembly and all are subject to material inconsistency and material fatigue.

The Oregon Orthotic system is a custom fabricated device that incorporates a rigid lamination technique that may include mechanical articulations for motion control. A further alternative is a Dynamic response AFO which incorporates a silicone matrix to provide increase flexibility in a custom fabricated device.

Hinged orthotic designs have been constructed in the past from either thermoplastics, laminates or metal with various hinge designs, in various configurations, and with different combinations of materials. These provided the orthotist an ability to alter motion control of the involved extremity using combinations of springs, elastic/urethane flexures or rigid mechanical stops, either fixed or adjustable. The mechanical hinged designs are subject to wear and noise. They also include a rigid stopping point that can impede a smooth, consistent motion through the stance phase of gait. The position of the mechanical stop is usually optimized for a stride length but cannot be varied with velocity or stride length. Hinged designs also tend to be bulky and heavy with the hinges placed on either medial, lateral or both sides of the ankle.

SUMMARY

An orthotic device includes a composite strut, a footplate removeably attached to a lower end of the strut, an upper tibial cuff removeably attached to an upper end of the strut and a lower tibial cuff removeably attached to a central portion of said strut. The strut, footplate, upper tibial cuff and lower tibial cuff are formed of a composite material, preferably a carbon fiber composite. Each of the footplate, upper tibial cuff and lower tibial cuff include a support structure molded into the component with threaded holes therein. The upper and lower end of the strut may also include mounting holes therein for bolting the upper tibial cuff and footplate thereto. Mounting structure may also include mounting plates positioned on the rear surface of the strut and one or more tapered wedges mounted between the mounting structure on a rear of the strut, said tapered wedges allowing an angled orientation of the footplate and cuffs in relationship to the surface of the strut to which it is attached.

BRIEF DESCRIPTION OF DRAWINGS

FIG. 12 shows a front view of an alternative wedge plate comprising a disc-shaped wedge with a single central hole.

FIGS. 13 and 14 are cutaway, side views taken along lines 13-13 in FIG. 12 showing adjacent disc wedges mounting a footplate horizontally or angled downward, respectively.

DESCRIPTION

Figure 1:
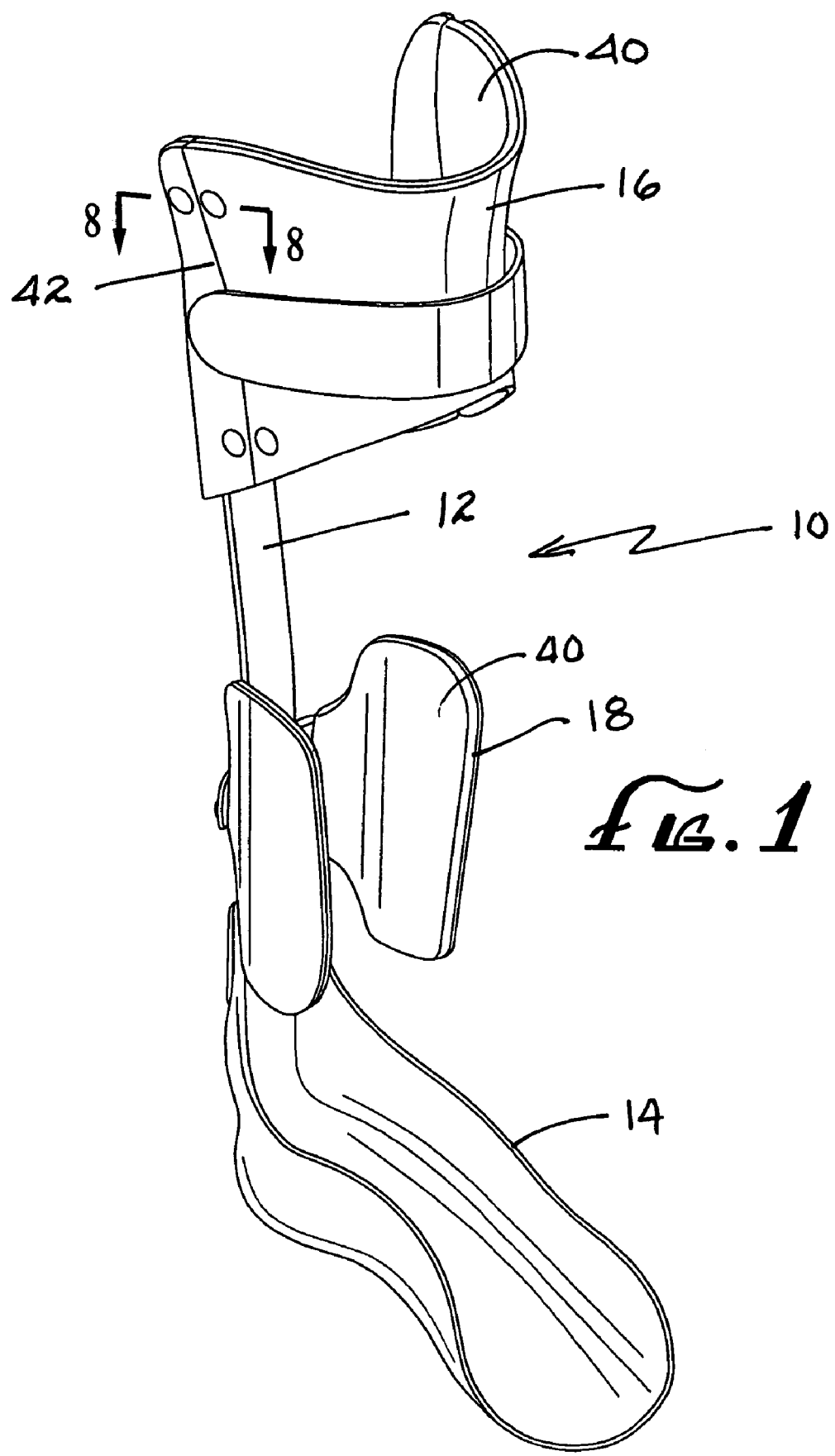
FIG. 1 is a front perspective view of the assembled DROCS incorporating features of the invention.
Figure 2:
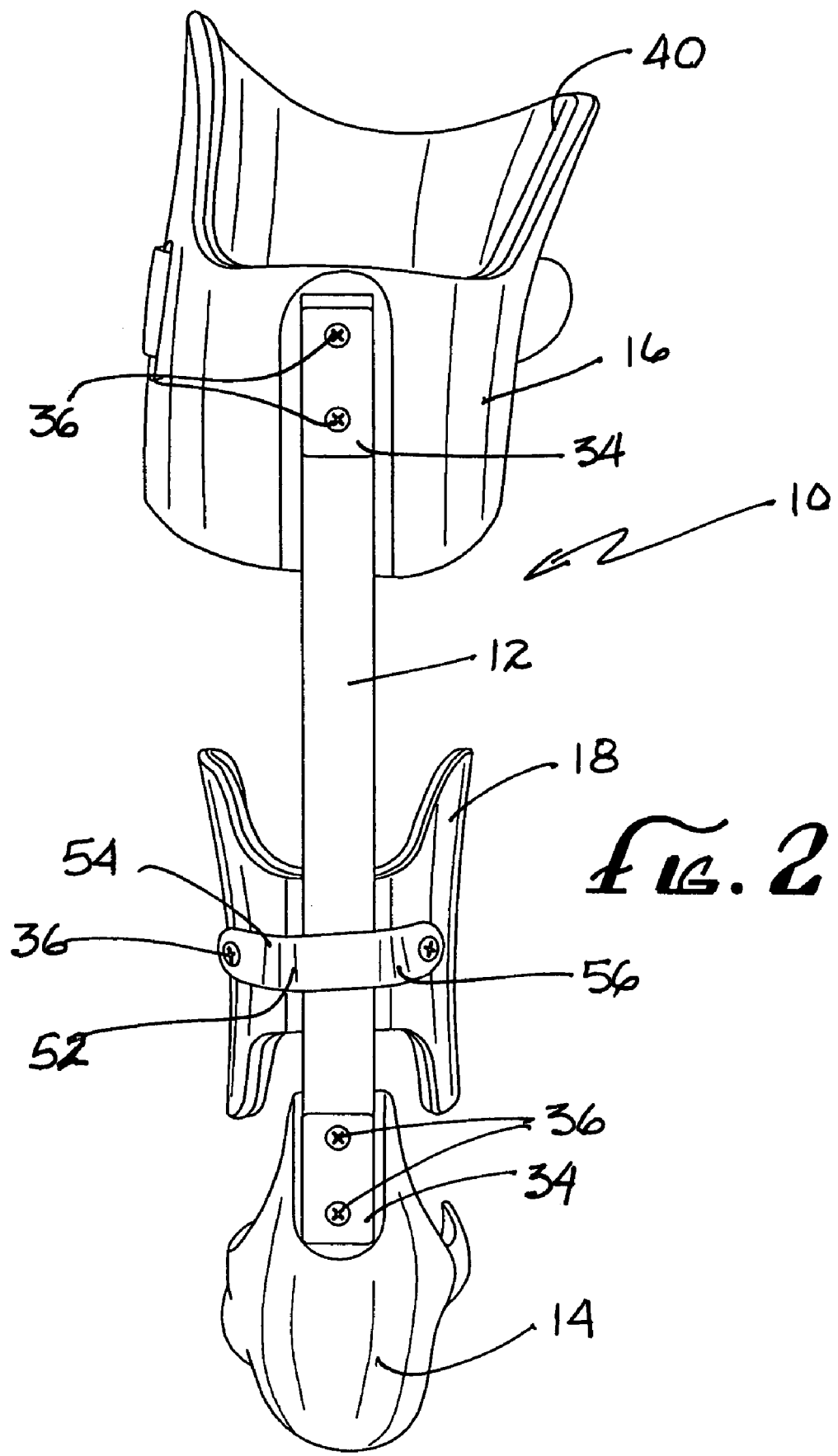
FIG. 2 is rear view of the assembled DROCS of FIG. 1.

The DROCS 10 is a modular component system which can be assembled into a custom fabricated orthoses by appropriately trained orthotists or prosthetists. It is applicable to Ankle Foot Orthoses (AFO), Knee Ankle Foot Orthoses (KAFO), Hip Knee Ankle Foot Orthoses (HKAFO) and Thoracic Hip Knee Ankle Foot Orthoses (THKAFO). One of the purposes of the device is to provide gait control, particularly in cases of knee, thigh, hip and pelvic muscular weakness in addition to dropfoot conditions. Such weakness may be present in, but not limited to, patients afflicted by stroke, spinal cord injury, fractures, multiple sclerosis, polio, muscular dystrophy or other neuromuscular or orthopedic injury. The DROCS 10 can provide increased gait efficiency, stability and velocity.

Various components assembled with specific components custom fabricated by an orthotist/prosthetis or licensed fabricator provide a completed leg brace. This device can be utilized following various neuromuscular weaknesses of the lower extremity. It can be applied in the acute, rehab or post recovery phases to aid and improve gait function. It is intended to allow normalized hip and knee motion during the gait cycles while maintaining the foot and ankle in a neutral position for swing phase toe clearance.

The DROCS 10 comprises a composite strut 12 with a footplate 14 and upper and lower tibial cuffs 16, 18 removeably mounted to the strut 12. The strut 12, as well as each of the components attached to it, can be sized and shaped (fabricated by composite forming techniques) to match the limb of the individual to which it is to be applied (contoured to follow calf muscle contours for cosmesis), or it can be assembled from standard sized components. Wedge shaped plates 20 or discs 62 can be utilized between the strut 12 and each of the attached components to further adjust the DROCS 10 for angle and tilt required for each patient and then readjusted as the patient gains mobility, adjusts to use of the DROCS 10 or the dimensions of the extremity changes, such as may occur as the patient exercises and rebuilds the muscle in the extremity.

The composite modular construction, particularly the use of the composite strut 12, described herein, provides several benefits over prior orthotic designs. Other orthotic designs use thermoplastic fabrications which are either custom fabricated to the individual patient or comprise pre-fabricated thermoplastic devices. These have advantages of light weight, ease of fabrication and relatively low cost. However, a disadvantage of these prior devices is a limited ability to control consistency in the thermoplastic components. This is due to extrusion and compounding differences, fabrication techniques and mold configuration which can alter orientation of plastic relative to the line of progression. Thermoplastic materials also have a poor ability to control transverse rotation under load. Thermoplastic devices tend to fatigue and are impacted by environmental changes such as temperature. These factors limit the ability of thermoplastic designs to be consistent in their use to stabilize transverse, rotary knee and ankle instabilities.

A curvalinear strut 12, preferably constructed using carbon, particularly graphite, fiber composites or other high strength, relatively stiff structural composite materials, provides dynamic controlled motion within the line of forward movement of the user. The strut 12 is contoured in a curvilinear shape to generally match the natural contour of the rear of a user's leg from ankle to below the knee (the calf of the lower leg). It provides resistance from mid thru terminal stance for tibial advance with a resultant increase in knee and hip stability while allowing a normalized knee flexion moment at heel strike through loading response. The strut 12 provides medio-lateral stability at the ankle while, at the same time, providing resistance to transverse rotation. Use of the composite material for construction of the strut causes it to provide an "energy storing" function. Unlike the traditional, simple, passive, leaf spring devices, this composite structure creates an "energy storing" function to supplement for muscular weakness of the calf, thigh and hip providing a normalized gait. Composite modular design further allows consistently controlled resistance. The composite is not adversely affected by temperature, humidity or fatigue as are thermoplastic AFO devices. Also, there are no moving parts subject to wear or rigid mechanical stopping points as in mechanically articulated designs to adversely impact gait.

The struts are approximately 1 cm to 3 cm in width and approximately 2 mm to 8 mm in thickness. Overall length is approximately 20 to 45 cm depending primarily on the patient's height and heel to knee distance. Strut dimensions are also determined by rigidity desired and the patient's height, weight and anticipated activity level. The degree of muscular weakness present and the clinical judgment of the orthotists/prosthetists using the component will further impact the strut dimension and shape selection process. It has been found that three different sizes, each size fabricated in three different stiffnesses from the most flexible to the most rigid, for a total of nine different struts 12, generally meet the full range of patient variables. The dimensions of these standard struts are selected based on the average adult population but can also be constructed in pediatric and children sizing. The bottom margin of the strut is contoured so that varus/valgus adjustments can be made.

The modular design of the DROCS 10 allows the strut 12 and the various components described herein to be varied to adjust the rigidity of the device as an individual patient's strength and gait function improve or decline depending upon diagnosis. The modular structure also accommodates for weight changes by replacement of the footplate 14 and the upper and lower tibial cuffs (the varus/valgus control cuff 16 and proximal tibial component 18) which can be custom fabricated to fit each individual. In addition, the modular construction allows the performance of the device to be tuned to the patients needs at any given point within the useful life of the device, or for damaged or worn components to be replaced, thus saving replacement costs.

A cast mold or digitally scanned image is typically taken of the individual's involved extremity. End user height, weight, and activity levels as well as extent of neuromuscular deficit are factors used to determine the optimal strut rigidity and size of the inverted "Y" reinforcing stirrup 22 which is molded into the footplate 14.

The custom components (footplate 14, varus/valgus control cuff 16 and proximal tibial component 18) for the end user are fabricated with the appropriate attachment components imbedded. The preferred fabrication method uses a carbon graphite lamination process. Upon lamination, trim lines appropriate for the end user's requirements are determined and all parts are prepared for final assembly.

Figure 3:
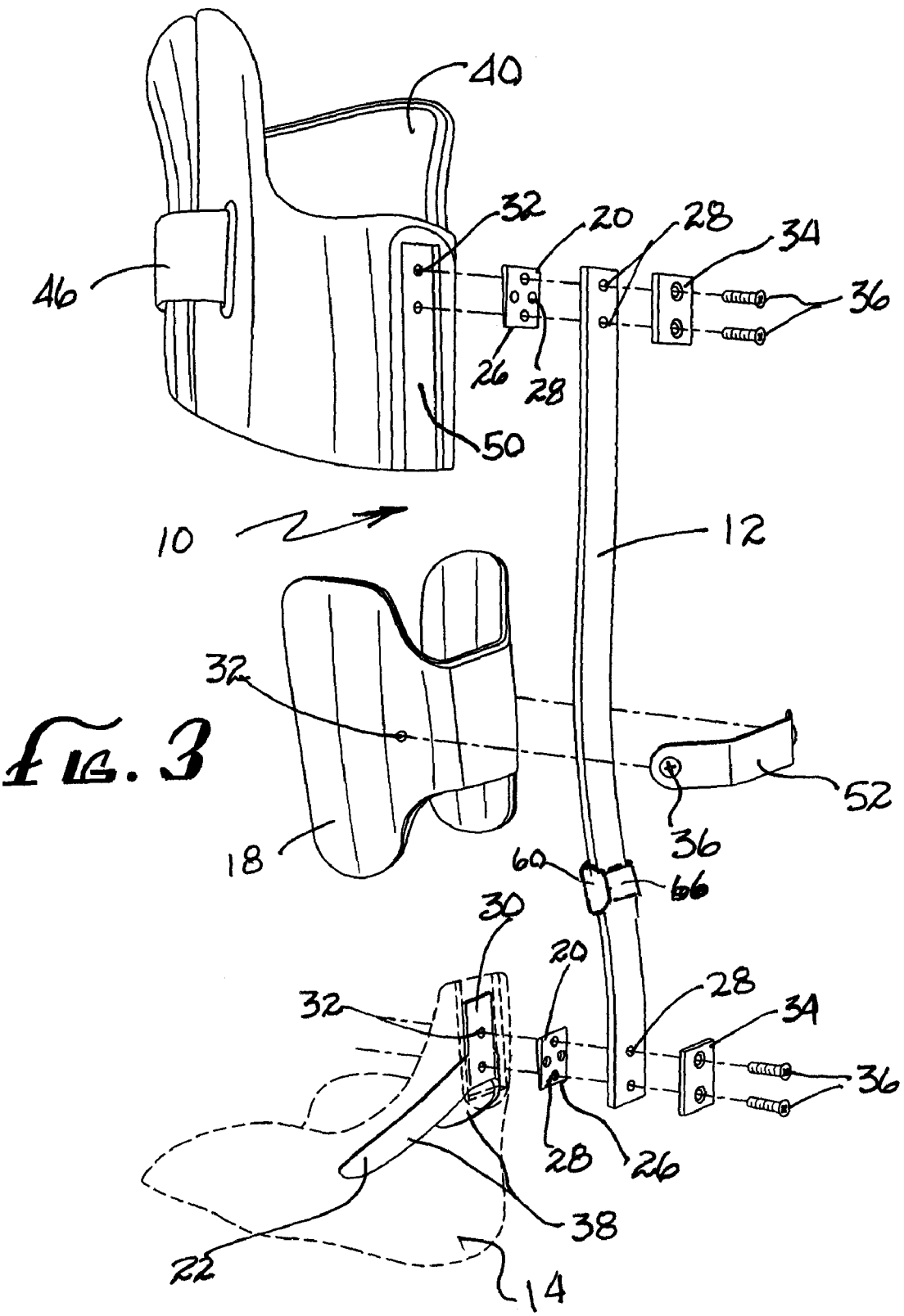
FIG. 3 is a side perspective exploded view of the components of the DROCS of FIG. 1 with the stirrup inside the footplate visible.

Fitting and alignment are adapted for each end user. During this stage the final adjustments are made for the end user. These adjustments may include angulation changes and rotary position changes relative to the line of progression and are made to optimize performance and gait function for the end user. These are accomplished by placement and orientation of the wedge plates 20 between the attachment components on each custom footplate and cuff 14, 16, 18 and the strut 12 and then attaching the upper and lower tibial cuffs 16, 18 to the strut 12 using a rearward positioned attachment plate 34 and bolts 36 through aligned holes 28, 32 in each component. For example, as shown in FIG. 3, the wedges 20 are positioned with the thin edge 26 downward. However, the wedges are substantially square and have four mounting holes 28, preferably in a square pattern as shown in FIGS. 6a, 6b, 6c, and 6d, located so that either opposite pairs of mounting holes 28 can be used. This provides the ability to orient the wedge 20 either vertically or horizontally with the thin end 26 pointing up, down, right or left as shown in FIGS. 6a, 6b, 6c, or 6d. By altering the thickness and placement of the wedge plates 20, either on the anterior or posterior aspect of the strut assembly, the performance characteristics of the strut can be altered to better suit the individuals requirements. The various sizes of wedge plate 20 allow alteration of plantar and dorsiflexion angulation to optimize device function and gait performance. They can be applied to the foot attachment and/or the tibial cuff assembly to re-orient the foot internally or externally relative to the line of progression and/or the plane of the strut assembly.

Use of wedge plates 20 oriented in any of the four directions and positioned adjacent the attachment component on the stirrup 22 in the footplate 14 provides the ability to rotate the footplate 14 relative to the line of progression and the plane of the strut 12. It also allows rotation of the footplate 14 relative to the tibial cuffs for gait optimization and/or comfort reasons.

As an alternative the square wedge plates 20 can be replaced by singular, paired or multiple circular wedge discs 62, shown in FIGS. 12 and 14. The wedge discs 62 have a single hole 68 in the middle to receive a bolt 36. Rotation of the discs 62 around the bolt 36 inserted in hole 68 in or through the paired discs 62 as shown in FIGS. 13, 14 will cause the attached footplate 14 to be angled downward, upward, left or right.

A typical wedge disc 62 is about ¾ to about 1¼ inches in diameter, about ⅛ inch thick and has a taper from one edge to an opposite edge of up to about 5°. However, a greater taper may be used as long as appropriate changes are made in the other dimensions of the disc to accommodate the greater angle. In the embodiment shown, the bolt 36 is inserted in a countersunk hole 28 in the footplate 14, through one or more stacked tapered discs 62 and secured by a tapered nut 70 or a threaded hole 32 in a rear plate 52. A typical bolt is 3/16 inches or greater in diameter, the hole 68 in the tapered disc 62 being larger in diameter to accommodate the bolt 36 when the discs 62 are rotated, as shown for example in FIG. 14, to provide the maximum intended angulation of the footplate 14.

Figure 4:
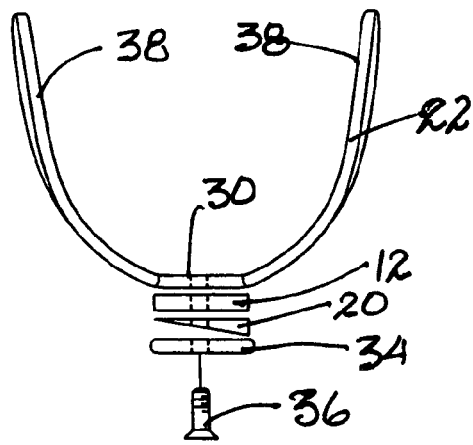
FIG. 4 is an exploded top view of the Y-stirrup as it appears mounted to the support brace.
Figure 6A:
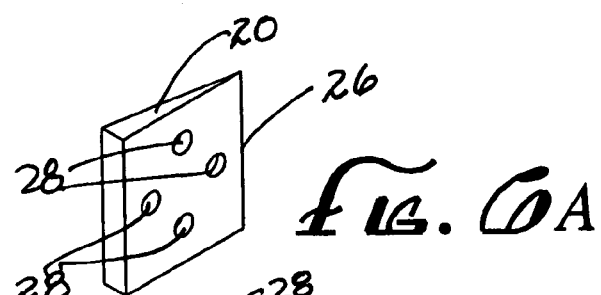
FIGS. 6a, 6b, 6c and 6d show shims used in the assembly in four different orientations.
Figure 6B:
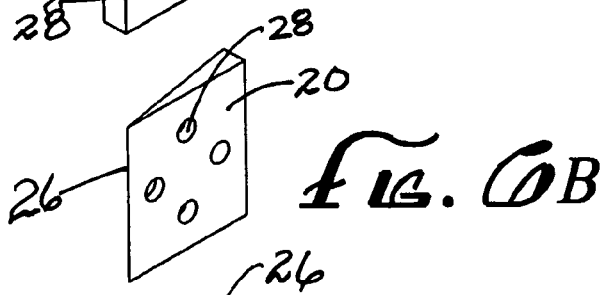
Figure 6C:
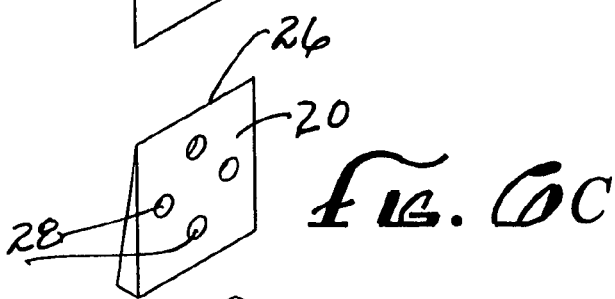
Figure 6D:
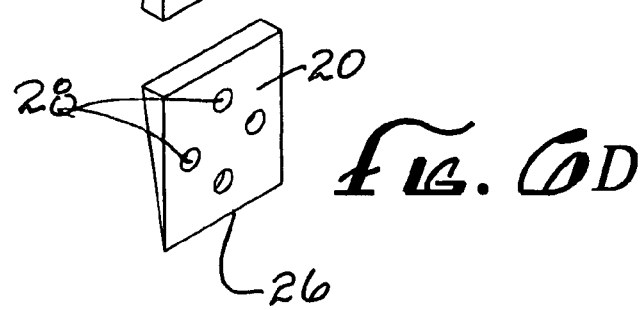
Figure 5:
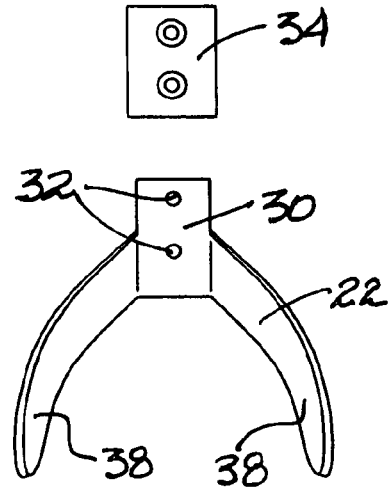
FIG. 5 is a front top view of the Y-stirrup of FIG. 4 along with its backing plate.

Footplate attachment: Referring to FIGS. 3-5, the footplate 14 comprises a composite structure which is shaped to fit the sole and sides of an individual's foot to provide surrounding support. It includes a Y-stirrup 22 which is molded into the footplate 14. The Y-stirrup 22 includes a U-shaped ankle support portion with a baseplate 30 at the base of the U for attachment of the Y-stirrup 22 to the lower end of the strut 12. The base plate 30 has two threaded holes 32 therein along a vertical center line located to match similar spaced holes 28 in the lower end of the strut 12. The U-shaped ankle support portion of the Y-stirrup 22 angles downward from the baseplate 30 toward the position of arch of the patient's foot at an angle of from about 45° to about 60°. Attachment plate 34 in concert with the bolts 36 and wedges 20 allow adjustable mounting of the footplate 14 with included inverted "Y" reinforced stirrup 22 to the strut 12. When applied to an individual's leg, the plate 34 and end of the strut 12 are positioned above the heel portion of the average adult shoe to minimize bulk within the shoe and resultant fitting problems. It allows angular changes to be made through insertion of one or more adjustment wedge plates 20 or discs 62 to either dorsiflex or plantarflex, internally or externally rotating the footplate.

The inverted "Y" stirrup 22, preferably fabricated from stainless steel, titanium or a reinforced composite matrix, is pre-contoured and pre-drilled and treaded for bolt 36 attachment to the strut 12. The arms 38 of the Y stirrup 22 are shaped to accommodate varied calcaneal widths and foot sizes. They are varied in dimension with 3 different sizes being adequate for the seven different struts 12. The inverted "Y" stirrup 22 is designed for differing patient size, weight and activity levels. The larger sizes are intended to accommodate the increased forces generated by the more rigid strut assemblies.

Proximal tibial component: While the upper and lower proximal tibial cuffs 16, 18 can be prefabricated, they preferably are custom formed from composite materials for each specific patient's particular requirements.

Figure 7:
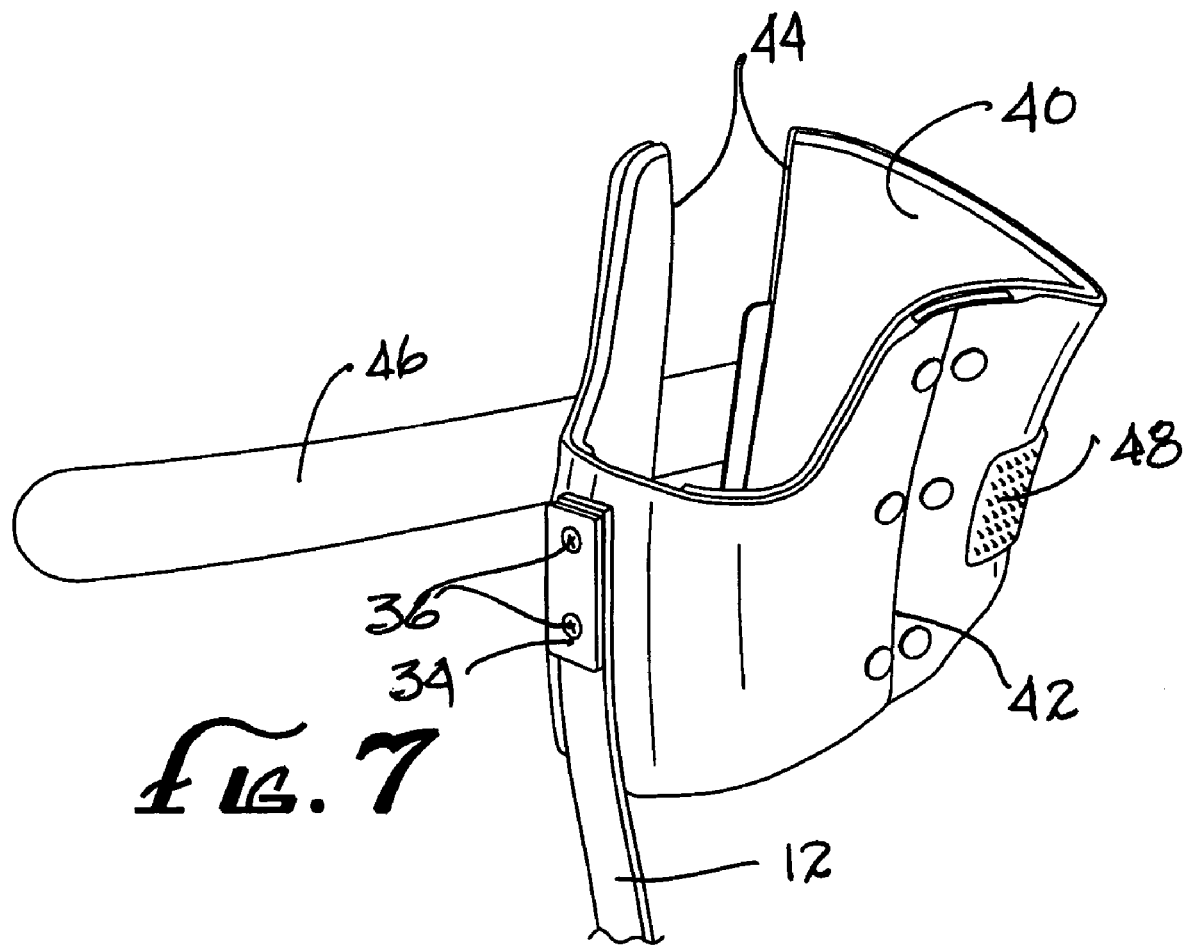
FIG. 7 is a perspective view of the proximal tibia support in its open configuration.
Figure 8:
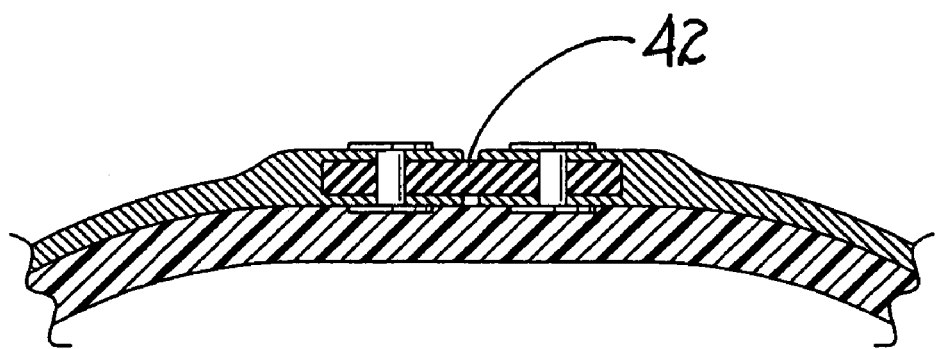
FIG. 8 is a cutaway view, along line 8-8 of FIG. 1, of the hinge portion of the proximal tibia support of FIG. 7.
Figure 9:
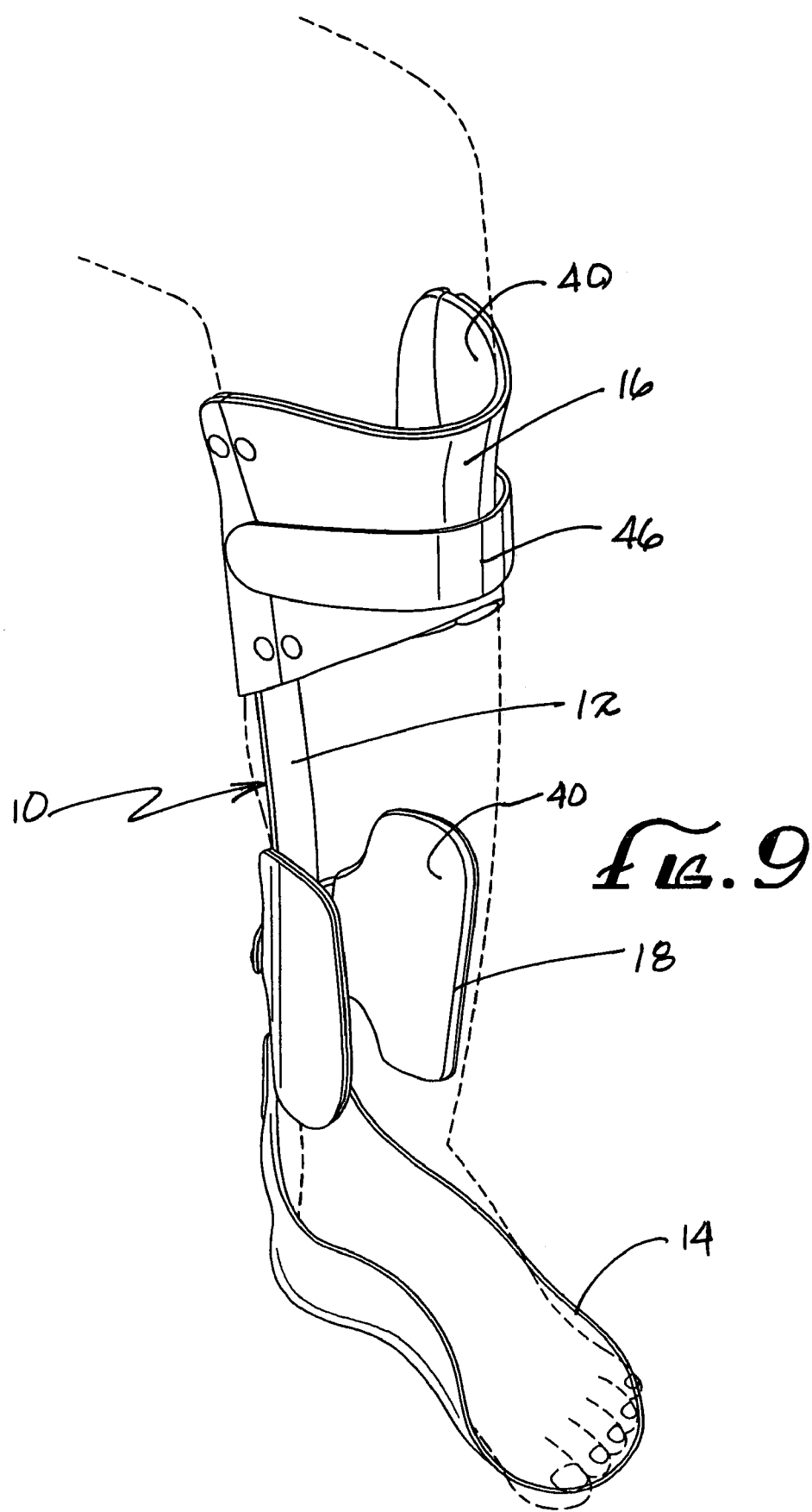
FIG. 9 is a front perspective view of the assembled DROCS of FIG. 1 mounted on the leg of a user.

The upper tibial cuff 16 is sized, in its closed configuration, with an inner diameter, including a cushioned liner 40, to provide a snug but non-constricting, encircling support for the leg of the patient just below the knee (see FIG. 9). It includes a vertically oriented hinge structure 42 in one side of the cuff 16, as best shown in FIGS. 7 and 8, and, on the opposite side of the encircling support, a vertical opening 44 which is minimized after placement on the leg and secured in a closed orientation, as shown in FIG. 9, by a latch or the two components of Velcro hook and loop fastener 46, 48. The cushioned liner 40 may be formed from numerous cushioning materials such as resilient foam or silicone rubber and can also include a soft fabric skin-contacting surface which allows the skin to breathe and prevents abrasive or moisture injury to the skin.

Mounted half-way between the hinge 42 and the opening 44 is a vertically oriented cuff base plate 50 which includes two vertically oriented threaded holes 32 for mounting the upper cuff 16 to similarly positioned holes 28 in the top end of the strut 12 using bolts 36 and attachment plate 34. A typical upper cuff 16 has a diameter of from about 2 inches to about 7 inches, typically 4-6 inches, and a vertical dimension of from about 1.75 inches to about 6 inches in its longest dimension.

The lower cuff 18 is sized to enclose the rear and sides of a central portion of the lower leg, providing a snug but non-constricting sleeve with an open front surface. The front opening and width of the cuff 18 approximate the size of the leg portion. The lower cuff 18 also includes an inner cushioned liner 40 of materials and construction similar to that used on the upper cuff 16.

Centrally located and molded into the lower cuff 18 is a mounting plate (not shown) which includes two horizontally aligned threaded holes 32 spaced apart a distance greater than the width of the strut 12. The lower cuff 18 is mounted to the strut 12 by a rear plate 52 having a flat central portion with a width approximating the width of the strut 12 and left and right wings 54, 56, each with holes such that bolts 36 placed there through can be screwed into the threaded holes 32 in the lower cuff 18 with the strut 12 sandwiched between the rear surface of the cuff 18 and the central portion of the rear plate 52. The arrangement of components allows the lower cuff 18 to be adjusted to a desired height along the length of the strut 12 and then locked into that location by tightening the bolts 36.

The rigid carbon graphite lamination technique provides comfortable transfer of forces generated by the composite strut 12 through the upper and lower tibial cuff 16, 18 directly to the users calf for an AFO design. Knee hinge attachments (not shown) can be incorporated into the assembly to create a (H)KAFO design. The attachment hardware allows adjustment of the tibial cuffs for individual comfort needs through height adjustment along the length of the strut. Coronal plane angulation may further be adjusted by incorporating appropriate adjustment wedge plates 20. Line of progression orientation may be altered via wedge plate 20 or disc 62 placement either on medial or lateral strut surfaces.

The attachment hardware, through alteration of trim, can also be used to further alter the rigidity of the strut assembly and its functional characteristics.

Figures 10, 11:
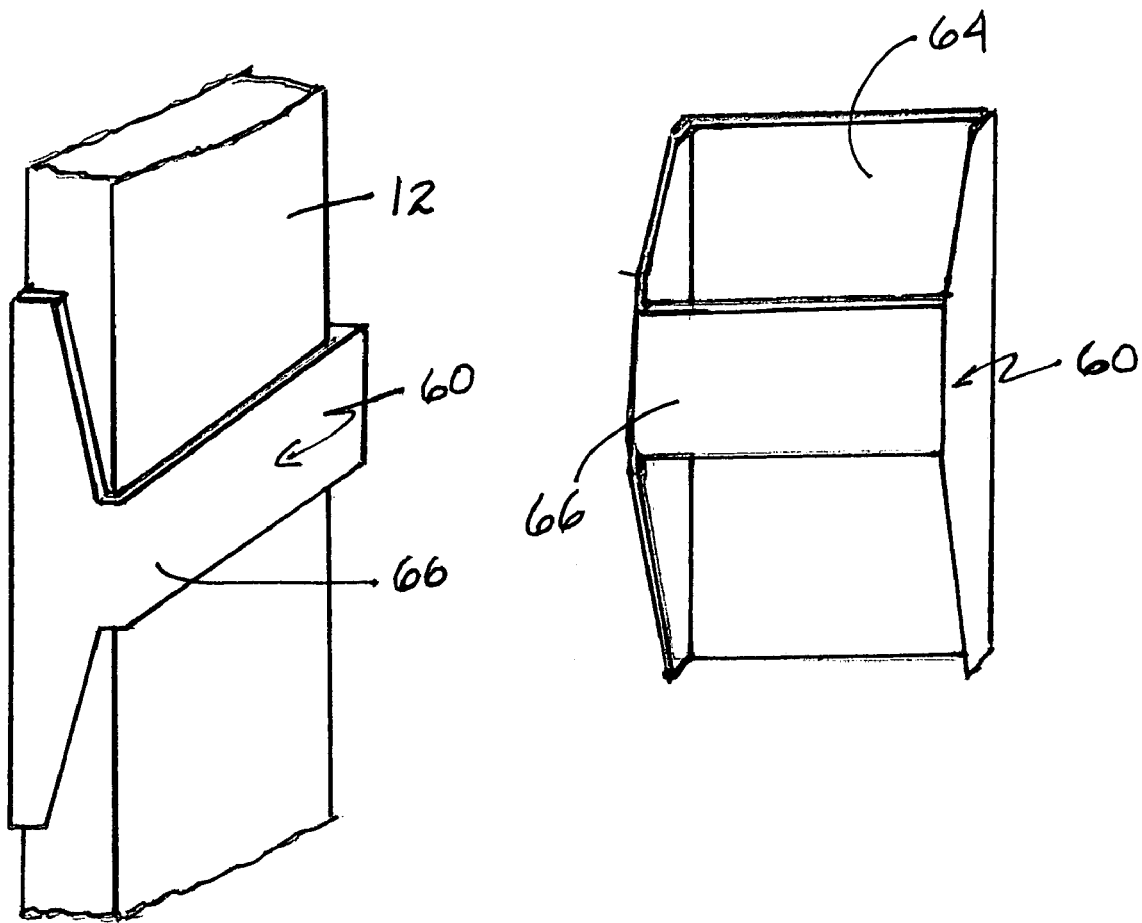
FIG. 10 is a front perspective view of a stiffening clip.
FIG. 11 is an enlarged side perspective view of a portion of the strut with the optional stiffening clip attached thereto.

As a further alternative, adjustment clips 60 can be added to the strut 12 to provide further adjustment to meet the user requirements for improved gait dynamics. These clips 60 attach to or slide over the strut so that flexibility of the existing strut is further limited in one direction and maintained via the strut rigidity in the opposing direction. For example, a clip can be placed such that plantar-flexion resistance is based upon the original strut rigidity. Placing the adjustment clip on the anterior aspect as shown in FIGS. 3 and 10 will increase the strut rigidity against dorsiflexion and not alter plantarflexion resistance. Alternatively the clip can be reversed into the posterior position to increase strut resistance against plantarflexion and leave the strut resistance into dorsiflexion unaltered. This is accomplished, as best shown in the enlarged view of FIGS. 10 and 11 by providing a clip 60 which slides over the strut, the clip 60 having a first longer face 64 and a second, shorter face 66, the longer face 64 retarding bending when the strut is flexed against that face.

To use the DROCS 10, the strut 12 length, shape and stiffness is selected to match the patient's stature, medical condition and physical activity level. An appropriate preformed footplate 14 and upper and lower tibial cuffs 16, 18 are selected. In the alternative, molds of the patient's foot and lower leg are made and custom footplate 14, upper cuff 16 and lower cuff 18 are fabricated to specifically match the patient's leg. The DROCS 10 is then assembled by bolting the footplate 14 and the upper cuff 16 to the strut 12 and loosely attaching the lower cuff 16 to the strut 12 so that its height can be easily adjusted. The assembled DROCS 10 is then applied to the patient's leg and, with the patient standing, the upper cuff 14 is secured using the Velcro fastener 46, 48. The height of the lower cuff 16 is then adjusted and it is secured to the strut 12.

Attachment bracket components: Additional brackets and hardware components (not shown) for attachment of custom sub-assemblies fabricated by the orthotists/prosthetists or licensed fabrication facility can be added to the DROCS 10. Bracket attachment allows removal and repositioning of sub-assemblies for improved user comfort, gait efficiency and device performance. For example, the brackets may be used for attachment of varus/valgus control modifications, varus/valgus control straps, heel retention straps, hip rotation control straps, etc.

Advantages of the DROCS system are its lightweight, modular construction allowing for interchange of struts, replacement of individual components and "fine tuning" of the positioning, orientation, dimensions, and stiffness or flexibility to meet the individual end user/patient physical and stature requirements. Lighter weight and lower profile footplate attachments provide cosmesis and a reduction in shoe bulk. The prefabricated design of the components provides greater reproducibility of fit and performance across patient groups with more consistent, predictable functional outcomes. The linear deflection of the composite strut allows consistent function despite environmental changes. Since there are no mechanical pivots, hinges or other moving parts, maintenance is reduced. The dynamic "energy storing" function can be utilized in optimizing gait for end user needs. The progressive resistance allows varying walking speeds to be enjoyed by the end user unrestrained by rigid gait motion limiters which function best at a single walking speed/stride length.

A variety of struts 12 with varied flexibility in dorsi and plantar flexion can also be provided. These variations allow increased resistance in one direction with a reduced resistance in other directions to further fine tune the device for the end user.

As a further variation, the contour, shape, and dimensions of the tibial cuffs can be varied to enhance gait control characteristics. The orthotists/prosthetists or fabrication facility can alter these compounds or may choose to omit the lower tibial cuff according to the individual end user's requirements. Various pads and/or straps may also be attached to this component to further optimize control and gait function based upon individual neuromuscular requirements. Also, while the preferred assembly includes an attachment plate 34, the invention contemplates assembly without that plate. Also, while the preferred embodiment includes holes in the upper and lower ends of the strut, other means may be used to secure the footplate 14 and upper cuff 16 to the strut 12. For example, a rear plate 52 such as used to moveably secure the lower cuff 16 or other securing structures may be used as an alternative. Also, while FIGS. 1-9 show the bolt head on the rear of the assembly, it is also contemplated that the bolt head can be in a countersunk hole on the rear surface of the attached component (i.e., footplate or cuff). Additionally, grooves, pins, notches or other structures can be attached to or molded in to the strut at various locations to aid in positioning the attached components and preventing those components from slipping or rotating once the system is assembled.

We claim:

1. A modular ankle foot orthotic system for securing to a patient's leg below the knee comprising
   a) a composite strut approximating the contour and length of the rear of the calf of the lower leg of the patient,
   b) a footplate formed of a composite material shaped to substantially conform to a lower surface, sides and heel of the patient's foot, said footplate including a Y-shaped stirrup formed from a structural material molded therein, the open end of the Y-shaped stirrup angled downward from an ankle area of the footplate to an arch of the footplate, the footplate being secured to a lower end of the strut,
   c) an upper tibial cuff sized to encircle the upper portion of the lower leg of the patient below the knee in a snug manner, the upper tibial cuff being secured to an upper end of the strut,
   d) a lower tibial cuff shaped to conform to the rear and sides of the patient's mid-calf area, the lower tibial cuff being secured to a central portion of the strut in a moveable manner, and
   e) attachment components and wedge plates or discs which taper to a thinner end for securing the footplate and upper and lower cuffs to the strut, the wedge plates providing angulation to the footplate and cuffs once secured to the strut, said orthotic system assembled by sandwiching one or more wedge plates between the strut on a first side and each of the positioned Y-shaped stirrup, upper cuff and lower cuff on a second side of the wedges.

2. The ankle foot orthotic system of claim 1 wherein the composite material used in forming the strut and footplate includes carbon fibers.

3. The ankle foot orthotic system of claim 1 wherein said strut has one or more mounting holes in the upper and lower ends thereof for securing attachable components thereto.

4. The ankle foot orthotic system of claim 1 wherein the attachment components comprise bolts and mounting plates.

5. The ankle foot orthotic system of claim 1 wherein the Y-shaped stirrup has a mounting plate integral therewith, the mounting plate including threaded holes positioned to align with holes in a rear attachment plate and the lower end of the strut.

6. The ankle foot orthotic system of claim 1 wherein the wedge plates have one or more mounting holes there through.

7. The ankle foot orthotic system of claim 1 wherein the wedge plates have at least four mounting holes there through arranged in a square pattern, the holes located at the corners of said square pattern and spaced so that when the orthotic system is assembled each pair of oppositely positioned holes aligns with holes in a rear attachment plate, the lower end of the strut, the mounting plate on the Y-shaped stirrup, or holes in a mounting structure molded into the cuffs.

8. The ankle foot orthotic system of claim 7 wherein the wedge plates can be positioned with the thinner end pointing downward, upward, left or right in relationship to the orientation of the strut.

9. The ankle foot orthotic system of claim 1 wherein the upper and lower cuff are formed of a composite material and include an inner cushioned liner.

10. The ankle foot orthotic system of claim 9 wherein the composite material includes carbon fibers.

11. The ankle foot orthotic system of claim 1 wherein the lower cuff is secured to the strut using a back plate wider than the width of the strut, the back plate having left and right holes therein spaced apart a distance greater than the width of the strut and aligning with threaded holes in a mounting plate molded into the lower tibial cuff such that placement of bolts in the aligned holes secures the back plate to the lower tibial cuff with the strut sandwich therebetween.

12. The ankle foot orthotic system of claim 1 wherein the wedge discs taper to a thinner edge and each disc has one hole therethrough.

13. The ankle foot orthotic system of claim 12 wherein at least two wedge discs are positioned in contact with the hole therethrough aligned so that the discs can be rotated around a bolt through said holes such that the positional relationship of the thin edge of each disc can be varied to adjust the orientation of attached components.

14. An ankle foot orthotic comprising a composite strut, a custom formed footplate removeably attached to a lower end of the strut an upper tibial cuff removeably attached to an upper end of said strut and a lower tibial cuff removeably attached to a central portion of said strut, the orthotic further including one or more tapered wedges or discs positioned between a mounting structure on a rear portion of one or more of the footplate, upper tibial cuff and lower tibial cuff with the mounting structure adjacent a first surface of the tapered wedge or disc, a second surface of the wedge or disc which is opposite the first surface adjacent a surface of the strut, said tapered wedge or disc angling the orientation of the footplate and cuffs in relationship to the surface of the strut to which it is attached.

15. The ankle foot orthotic of claim 14 wherein the footplate, upper tibial cuff and lower tibial cuff are formed of a composite material.

16. The ankle foot orthotic of claim 14 wherein the strut, footplate, upper tibial cuff and lower tibial cuff are formed of composite material comprising carbon fibers.

17. The ankle foot orthotic system of claim 14 wherein said strut has mounting holes in the lower and upper ends thereof for securing the footplate and upper tibial cuff thereto.

18. The ankle foot orthotic system of claim 14 further including bolts and mounting plates for securing the footplate, upper tibial cuff and lower tibial cuff to the strut.

19. The ankle foot orthotic system of claim 14 wherein the footplate is formed of a composite material shaped to substantially conform to a lower surface, sides and heel of the patient's foot, said footplate including a Y-shaped stirrup molded therein, the open end of the Y-shaped stirrup angled downward from an ankle area of the footplate to an arch of the footplate, the Y-shaped stirrup including mounting structure on the rear thereof for secured the footplate to the lower end of the strut.

20. The ankle foot orthotic system of claim 19 wherein the mounting plate includes threaded holes positioned to align with holes in a rear attachment plate and the lower end of the strut and bolts in the aligned holes for securing the footplate to the strut.

21. The ankle foot orthotic system of claim 14 wherein the wedge plates or discs taper to a thin edge and the wedge plates or discs have one or more mounting holes there through.

22. The ankle foot orthotic system of claim 21 wherein the wedge plates have at least four mounting holes there through arranged in a square pattern, the holes being located at the corners of said square pattern and spaced so that when the orthotic system is assembled each pair of oppositely positioned holes aligns with holes in a rear attachment plate, the lower end of the strut, the mounting plate on the Y-shaped stirrup, or holes in a mounting structure molded into the cuffs.

23. The ankle foot orthotic system of claim 22 wherein the wedge plates or discs can be positioned with the thin edge pointing downward, upward, left or right in relationship to the orientation of the strut.

24. The ankle foot orthotic system of claim 14 wherein upper and lower cuffs are formed of a composite material, the cuffs having an inner cushioned liner.

25. The ankle foot orthotic system of claim 14 wherein the lower cuff is secured to the strut using a back plate wider than the width of the strut, the back plate having left and right holes therein spaced apart a distance greater than the width of the strut and aligning with threaded holes in a mounting plate molded into the lower tibial cuff such that placement of bolts in the aligned holes secures the back plate to the lower tibial cuff with the strut sandwich there between.

* * * * *